US00PP29799P3

(12) United States Plant Patent
Lee

(10) Patent No.: US PP29,799 P3
(45) Date of Patent: Nov. 6, 2018

(54) ***ILEX* PLANT NAMED 'BLH01'**

(50) Latin Name: *Ilex hybrida*
Varietal Denomination: BLH01

(71) Applicant: Robert Edward Lee, Independence, LA (US)

(72) Inventor: Robert Edward Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 5 days.

(21) Appl. No.: 15/530,929

(22) Filed: Mar. 24, 2017

(65) Prior Publication Data

US 2018/0279529 P1 Sep. 27, 2018

(51) Int. Cl.
*A01H 5/02* (2018.01)

(52) U.S. Cl.
USPC ..... Plt./247

(58) Field of Classification Search
USPC ..... Plt./247
See application file for complete search history.

*Primary Examiner* — Anne Marie Grunberg
(74) *Attorney, Agent, or Firm* — Cassandra Bright

(57) ABSTRACT

A new and distinct *Ilex* cultivar named 'BLH01' is disclosed, characterized by distinctive low growing, compact habit. Plants are very well suited for performance in the landscape, including as a specimen plant or a hedge. The new cultivar is a *Ilex*, suitable for ornamental garden purposes.

1 Drawing Sheet

Latin name of the genus and species: *Ilex hybrida.*
Variety denomination: 'BLH01'.

BACKGROUND OF THE INVENTION

The new cultivar is a product of a planned breeding program by the inventor, Robert Edward Lee. The inventor's intention was to develop ornamental *Ilex* plants with interesting compact plant habits and good landscape performance. This new variety, hereinafter referred to as 'BLH01', was discovered as a seedling, resulting from seeds collected form a large open pollination breeding program including many various species of *Ilex*. Parent varieties and date of the open pollination are unknown. Seeds were planted in Fall of 2005, with selection occurring the following year, and final selection made during 2010. The open pollination, planting and selection of the new variety all occurred at a commercial nursery in Independence, La.

After identifying the new variety as a potentially interesting selection, the inventor first organized propagation of 'BLH01' by vegetative cuttings Fall of 2007 at the same commercial nursery in Independence, La. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'BLH01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLH01' These characteristics in combination distinguish 'BLH01' as a new and distinct *Ilex* cultivar:

1. Unique low growing habit.
2. Compact plant.
3. Above average resistance to pests and diseases.
4. Tolerant of a variety of soils.
5. Plants very well suited for landscape use, including hedge planting or as a specimen.

COMPARISON TO PARENT VARIETY

Parent varieties are unknown.

COMMERCIAL COMPARISON

'BLH01' can be compared to the commercial variety *Ilex crenata* 'Dwarf Pagoda', unpatented. Plants of the new cultivar 'BLH01' are similar to plants of 'Dwarf Pagoda' in most horticultural characteristics, however, plants of the new cultivar 'BLH01' differ in the following:

1. 'BLH01' has an outwardly spreading plant habit, plants of 'Dwarf Pagoda' are narrowly upright.
2. Foliage of the new variety is small and narrow, foliage of 'Dwarf Pagoda' is smaller and round.

'BLH01' can be compared to the commercial variety *Ilex crenata* 'Soft Touch', unpatented. Plants of the new cultivar 'BLH01' are similar to plants of 'Soft Touch' in most horticultural characteristics, however, plants of the new cultivar 'BLH01' differ in the following;

1. 'BLH01' has solid dark green foliage, 'Soft Touch' has foliage with a silver mid-vein.
2. Foliage of 'BLH01' is strong and firm, foliage of 'Soft Touch' is soft and flexible.
3. 'BLH01' foliage upper surface is very glossy, surfaces of 'Soft Touch' are matte.

4. Foliage shape of the new variety is oblanceolate, foliage shape of 'Soft Touch' is more rounded.

BRIEF DESCRIPTION OF THE PHOTOGRAPH

The accompanying photograph illustrates in full color a 2 year old plant of the new variety in a 3 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLH01' plants grown outdoors in Loxley, Ala. Plants are approximately 2 years old, in a 3 gallon nursery container. Measurements and numerical values represent averages of typical plant types.

Botanical classification: *Ilex hybrida* 'BLH01'.

PROPAGATION

Typically by semi-hardwood cuttings in Spring and Summer.

Root description: Semi-woody, moderately dense roots. Colored near RHS Grey-Brown 199A.

PLANT

Growth habit: Semi-upright, outwardly spreading evergreen shrub. Low growing.

Height: Approximately 40 cm.

Plant spread: Approximately 75 cm.

Branching characteristics: Well branched, approximately 4 to 7 primary branches from the center of the plant. Branches occur at approximately 60° to 90° angles. Each primary branch has 4 to 10 lateral branches.

Primary branches:

Length of primary branches: Average range 15 to 25 cm, then branching into further laterals.

Diameter of primary branches: Approximately 6 mm.

Primary branch strength: Very strong, not flexible.

Primary branch color: Near RHS Greyed-Green 197C.

Primary branch texture: Glabrous, very minor roughness.

Lateral branches:

Number of lateral branches: Approximately 4 to 10 per primary branch.

Length of lateral branches: Average range 10 to 25 cm.

Diameter of lateral branches: Average 4 mm.

Lateral branch strength: Moderately strong.

Lateral branch color: Near RHS Grey-Brown 199D.

Lateral branch texture: Glabrous, smooth.

Internode length: Average 6 to 8 mm.

Age of plant described: Approximately 1 year.

FOLIAGE

Leaf:

*Type*.—Simple.

*Arrangement*.—Alternate.

*Average length*.—Approximately 1.6 cm.

*Average width*.—Approximately 0.7 cm.

*Shape of blade*.—Oblanceolate.

*Apex*.—Obtuse.

*Base*.—Attenuate.

*Attachment*.—Stalked.

*Margin*.—Finely serrate.

*Texture of top surface*.—Glabrous.

*Texture of bottom surface*.—Glabrous.

*Appearance of top surface*.—Very glossy.

*Appearance of bottom surface*.—Matte.

*Color*.—Young foliage upper side: Near RHS Green 137, but darker. Young foliage under side: Near RHS Green 138A. Mature foliage upper side: Slightly darker than RHS Green 139A. Mature foliage under side: Near RHS Green 137C.

*Venation*.—Type: Pinnate. Venation color upper side: Mid-vein near RHS Yellow-Green 151A. Venation color under side: Mid-vein near RHS Yellow-Green 151D, mid-vein indistinguishable from leaf blade.

*Petiole*.—Length: About 2 mm. Diameter: Less than 1 mm. Color: Upper Surface: Near RHS Yellow-Green 151A. Lower Surface: Near RHS Yellow-Green 151D.

FLOWER

Flowering not observed.

OTHER CHARACTERISTICS

Disease and pest resistance: Observed to be more resistant to normal diseases and pests of *Ilex*.

Temperature tolerance: USDA Zone 6 through 9.

Fruit/seed production: Not observed to date.

What is claimed is:

1. A new and distinct cultivar of *Ilex* plant named 'BLH01' as herein illustrated and described.

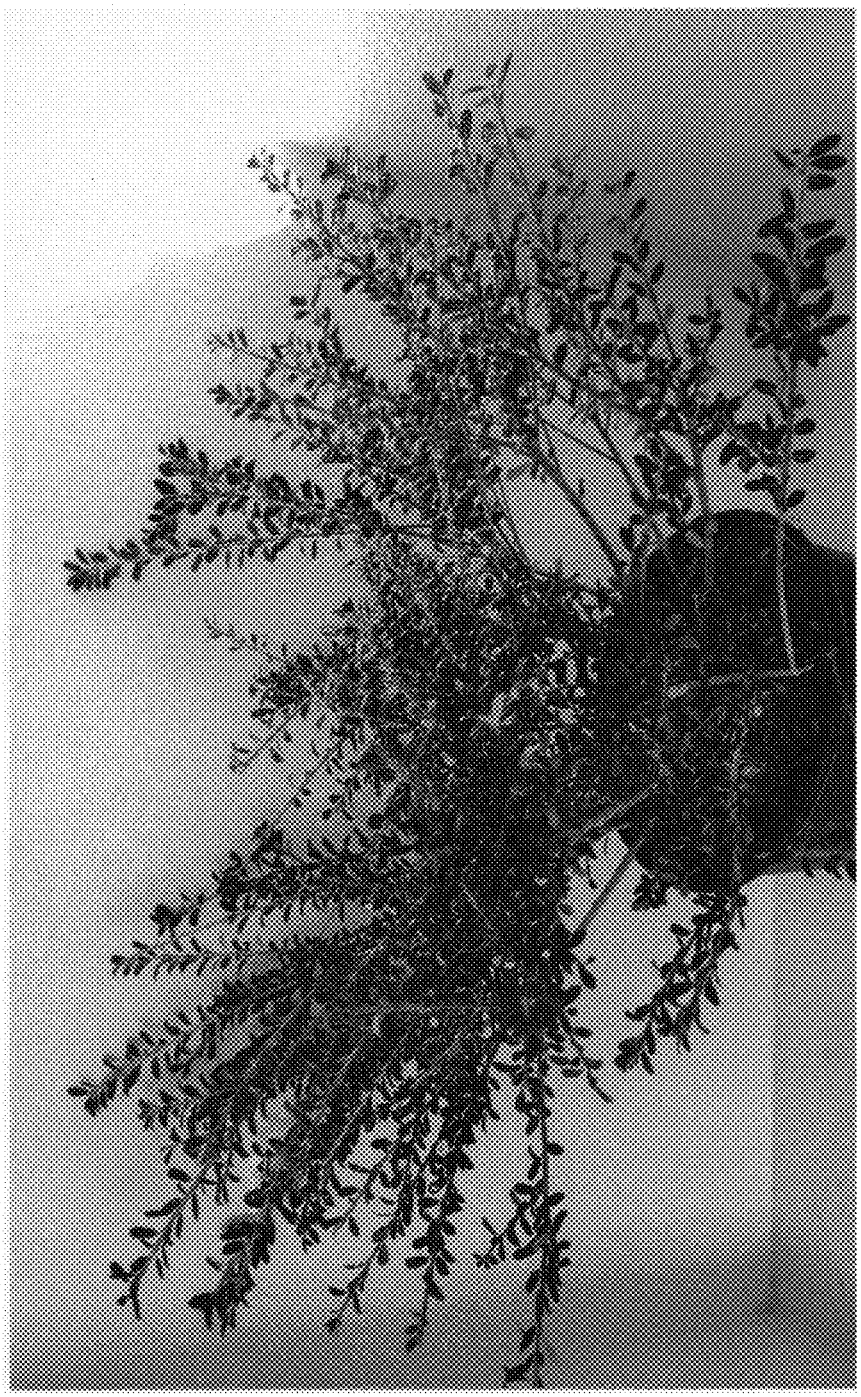

* * * * *